United States Patent [19]

Shippert

[11] 4,213,452
[45] Jul. 22, 1980

[54] COMPOUND SPLINT AND KIT

[75] Inventor: Ronald D. Shippert, Englewood, Colo.

[73] Assignee: The Denver Splint Company, Littleton, Colo.

[21] Appl. No.: 35,917

[22] Filed: May 3, 1979

Related U.S. Application Data

[63] Continuation-in-part of Ser. No. 813,800, Jul. 8, 1977, Pat. No. 4,153,051.

[51] Int. Cl.² ............................................. A61F 5/04
[52] U.S. Cl. ................................ 128/89 R; 128/76 C
[58] Field of Search ................ 128/89 R, 76 C, 87 R, 128/163, 132, DIG. 15

[56] References Cited

U.S. PATENT DOCUMENTS

| 3,742,943 | 7/1973 | Malmin | 128/76C |
| 3,835,848 | 9/1974 | Berner | 128/76 C |

FOREIGN PATENT DOCUMENTS 437661 12/1925 Fed. Rep. of Germany ........ 128/76 C

OTHER PUBLICATIONS

Alumafoam Nasal Splint, Conco Catalogue p. 12, Oct. 1972.

*Primary Examiner*—John D. Yasko
*Attorney, Agent, or Firm*—Sheridan, Ross, Fields & McIntosh

[57] ABSTRACT

A compound splint, primarily for use after nasal surgery, prevents edema fluid from splaying the bones apart so that they will grow back together and includes a base layer of adhesive tape applied directly to the nose, a secondary component of flexible material adhesively secured to the base layer and having an intertwining surface on its outer face, and a primary restraining component. The latter includes a panel of malleable metal and a layer of fabric secured to one face of the panel, the fabric having an interlacing surface. In use, the primary component is applied to the central portion of the secondary component with portions of the interlacing surface engaging central portions of the intertwining surface. The side portions are then pressed inwardly against the sides of the nose to the desired final shape with the remaining portion of the interlacing surface engaging the remaining portion of the intertwining surface. Thus the primary component is securely anchored in place and prevents any change in size or shape of the traumatized nose during recovery.

8 Claims, 10 Drawing Figures

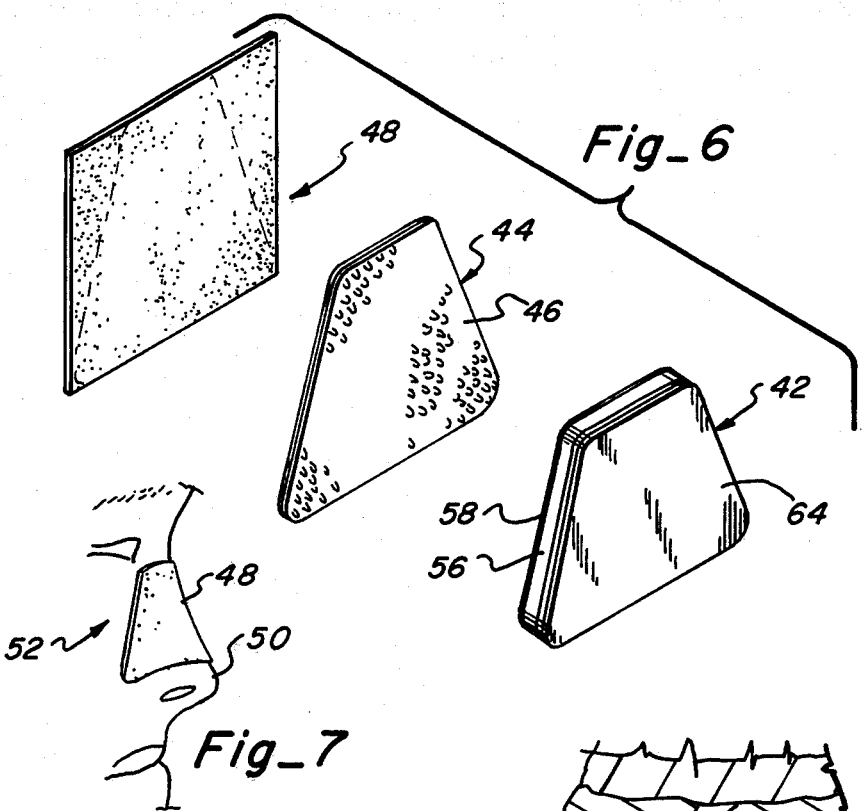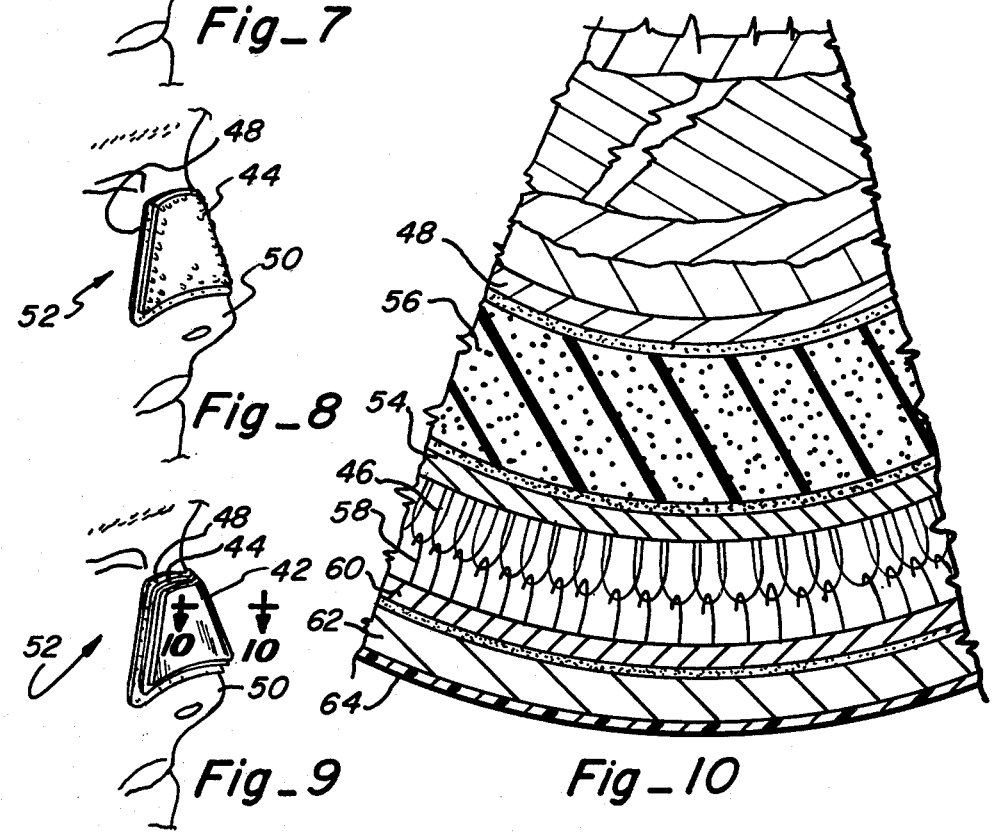

COMPOUND SPLINT AND KIT

DESCRIPTION

TECHNICAL FIELD

This application is a continuation-in-part of my co-pending application Ser. No. 813,800, filed July 8, 1977 now U.S. Pat. No. 4,153,051. The device of this invention lies in the field of splints or braces for application to traumatized portions of a human body and is directed more particularly to a device of this class which is useful in maintaining during the healing period a traumatized nose resulting from injury or surgery in the desired size and shape after squeezing out all of the edema fluid from the soft tissue.

BACKGROUND ART

For many years it has been common practice to form splints from Plaster of Paris for use in maintaining immobility of bony segments after surgery. They are difficult to make and difficult to retain in place, requiring excessive taping or bandaging, in addition to being uncomfortable and unsightly. Various other approaches have been tried with indifferent success.

One approach has been the molding of a complete face mask, the nose portion of which is then modified to the desired contour. One or more blanks of sheet material are then formed to fit the contour and secured to a restraining member. The device is placed over the nose and an elastic band connected to the ends of the restraining member is passed around the back of the head to hold the splint in place. An example of this type is disclosed in U.S. Pat. No. 3,742,943 to Malmin. Obviously the method is expensive and time consuming and the splint is easily displaced from its intended position.

In a somewhat similar approach a piece of malleable sheet metal of about the same area as the nose is laid against the nose and then pressed inward to assume the same shape as the nose. A retainer similar to a pair of goggles is applied to the splint and a headband connected to the ends of the retainer tends to hold it in place. An example of this type is disclosed in U.S. Pat. No. 3,835,848 to Berner. While the method of manufacture is simpler and cheaper than that of Malmin, it suffers from the same disadvantages in use. The device is uncomfortable and unsightly and the splint itself is easily displaced especially when the wearer is sleeping. Since neither of these devices is directly secured to the nose, they both fail to maintain constant pressure on precise areas to prevent swelling or distortion.

DISCLOSURE OF INVENTION

The device of this invention and its method of application overcome the difficulties and disadvantages mentioned above and provide a compound splint which is inexpensive in materials, easy to apply and form to the desired shape, and firmly anchored in position to perform its proper function.

Generally stated, the total compound splint includes a base layer, a secondary component, and a primary restraining component. The base layer may be a single piece of adhesive tape but preferably consists of a plurality of narrow strips of tape laid across the nose laterally with each successive strip overlapping the preceding one in the longitudinal direction and firmly pressed in place. The secondary component is preferably a layer of flexible material with a first face adapted to engage the tape and a second face provided with an intertwining surface. Either the first face of the secondary component or the exposed face of the base layer is provided with an adhesive coating and the secondary component is pressed into secured relation with the base layer.

The primary restraining component includes a malleable metallic panel and a flexible layer formed on a first face having an interlacing surface. The second face is adhesively secured to the metallic panel. To complete the installation of the splint the primary restraining component is placed in contact with the secondary component with the central portion of the interlacing surface engaging the central portion of the intertwining surface. The primary restraining component is then pressed inwardly against the two sides of the nose. The remaining portion of the interlacing surface engages the remaining portion of the intertwining surface and causes the edema fluid to be squeezed out of the soft tissue above the bones. When the panel is bent to a shape corresponding to that of the nose, substantially all of the interlacing surface is engaged with the intertwining surface and the panel is in position to firmly retain the nose in desired shape during recovery. Any swelling which takes place will now occur inwardly rather than outwardly due to the pressure of the splint so that the bones which are to knit together cannot be splayed.

In a first embodiment of the present invention, the intertwining surface includes a plurality of loops made from a coarse, woven fabric material while the interlacing surface has a multiple hook formation made from a relatively coarse material. The loops engage the hooks to sturdily hold the secondary component and primary restraining component together. In a second embodiment, the intertwining surface includes a fine, loose fibrous material which is capable of tightly engaging the hooks of the interlacing surface. A layer of foam is connected to the intertwining surface. It is readily understood that a plurality of embodiments can be devised. For example, the intertwining surface of the secondary component could include hooks of coarse material while the interlacing surface of the primary restraining component could include loose fibrous material. It being required only that the interlacing and intertwining surfaces fixedly engage each other so that the primary component is strongly held against the secondary component on the nose of the person.

BRIEF DESCRIPTION OF THE DRAWINGS

Various other advantages and features of novelty will become apparent as the description proceeds in conjunction with the accompanying drawings in which:

FIG. 6 is an exploded view of a second embodiment of this invention, showing the fine, loose fibers and hook arrangement;

FIG. 7 is fragmentary, side elevational view of a person's head, similar to FIG. 2, with the base layer comprising a tape pad in position;

FIG. 8 is a view similar to FIG. 3 with the secondary component in position;

FIG. 9 is a view similar to FIG. 4 with the primary restraining component in position; and FIG. 10 is a greatly enlarged lateral section, taken along line 10—10 of FIG. 9, showing details of the compound splint.

BEST MODE FOR CARRYING OUT THE INVENTION

Figure 2:
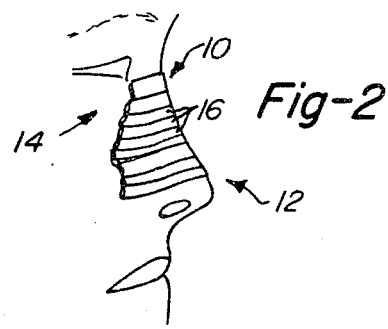
FIG. 2 is a fragmentary side elevational view of a person's head with the base layer comprising a plurality of strips in position.
Figure 3:
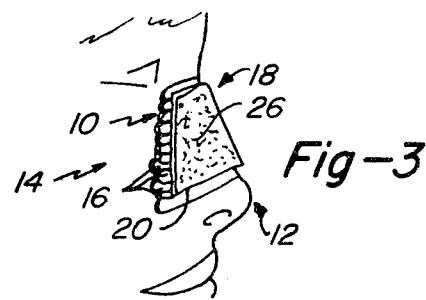
FIG. 3 is a view similar to FIG. 2 with the secondary component in position.
Figure 4:
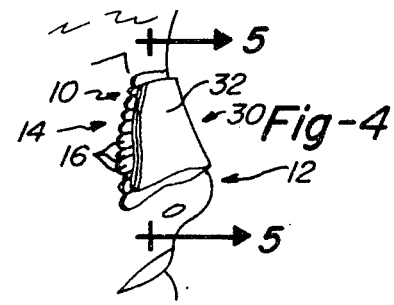
FIG. 4 is a view similar to FIG. 3 with the primary restraining component in position.

In accordance with this invention, a compound splint is provided which is securable to a traumatized nose. In a first embodiment, the compound splint and its application are schematically illustrated in FIGS. 2, 3, and 4, in which a base layer 10 is shown in position on the nose 12 of the person 14. The base layer, in preferred form, is produced by sequentially applying a plurality of strips 16 of adhesive tape, preferably paper, to the nose laterally, starting near the radix end with each successive strip overlapping the preceding strip in a longitudinal direction to the dome end, the strips extending to or slightly beyond the lateral osteotomy sites. The skin is first cleansed and dried, and then a coating of tincture of benzoin or the like is applied and also allowed to dry thoroughly before the tape is applied.

Figure 1:
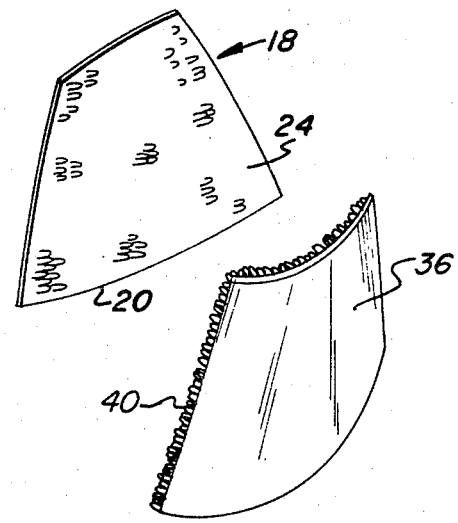
FIG. 1 is a perspective view of a first embodiment of this invention showing the coarse loops and hooks with their mating faces confronting each other.
Figure 5:
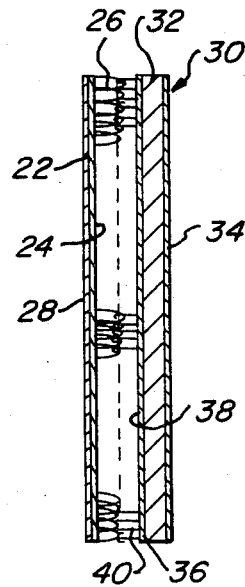
FIG. 5 is a greatly enlarged sectional view taken on line 5—5 of FIG. 4.

A secondary component 18 is shown in FIGS. 1 and 5 as being in the form of a thin flexible layer 20 of material such as woven fabric having a first face 22 adapted to be applied to the base layer and a second face 24 provided with an intertwining surface such as a multiple loop, hook-receiving, formation 26 which serves a dual purpose as a connector means and as a felt-like body made of relatively coarse material and having sufficient thickness to produce a cushioning effect. The first face is adapted to be adhesively secured to the base layer. The latter may have an adhesive coating but it is presently preferred to provide the adhesive coating on face 22 and protect it with a release sheet 28 until it is to be used. Component 18 is trimmed to a shape corresponding to that of the base layer but of less lateral and longitudinal extent so that when applied it will not extend laterally beyond the lateral osteotomy sites. The release sheet is stripped off and face 22 is pressed tightly against the base layer to be fixedly united thereto, as shown in FIG. 3.

The primary restraining component 30 is shown in FIG. 5 as being made up of a malleable metallic panel 32 having a coating of flesh-colored tape 34 on its exposed side and adhesively united on its second side to a layer 36 of flexible fabric provided on its exposed face 38 with an interlacing surface such as a multiple hook formation 40. Layers 20 and 36 with their loop and hook connector means are available on the market and are sold under several brand names including the trademark VELCRO. Component 30 is trimmed to have almost identically the same planform as component 18, being a few millimeters larger laterally and longitudinally to overlie the edges of component 18. Panel 32 is preferably made from a sheet of soft aluminum having a thickness of the order of sixteen gauge.

Component 30, in its flat form, is applied to panel 18 in such fashion that the vertically central portion of layer 36 contacts the vertically central portion of layer 20, and some of the hooks engage some of the loops. The side portions of component 30 are then gently but firmly pressed inward toward the sides of the nose until it assumes the same shape, with the remainder of the hooks engaging the loops progressively until all of component 30 is securely fashioned in place. As component 30 is pressed into place, the edema fluid will be squeezed from the soft tissue above the bony structure of the nose. Although panel 32 is malleable enough to be formed manually, it is adequately stiff enough to prevent any outward swelling or distortion of the nose during the recovery period, which would splay the bones before they begin to knit together. Thus, any swelling which occurs will be inward and therefore will not affect the healing process.

It will be apparent that the principal components may be prepared, stocked and sold in kit form in which the malleable panel 32, the hook formation layer 36, and the loop formation layer 20 are cut to a trapezoidal planform as shown. In such kit, layer 36 is already secured to one face of panel 32 and the flesh colored tape 34 is secured to its other face. Layer 20 has an adhesive coating covered with release sheet 28. The hook and loop formations are pressed together as shown in FIG. 5 to produce a simple and neat package which remains in its flat form until it is to be used. At that time the hook and loop formations are separated, the release sheet is stripped off, and the secondary component is ready to be mounted in position. The tape strips are readily available in any medical office or hospital and need not be supplied with the kit. In some cases the tape is not used, and layer 20 may be applied directly to the skin. The trapezoidal shape conforms to the area of the nose to be covered and may be supplied in a variety of sizes so that special trimming will seldom be necessary.

In a second embodiment as illustrated in FIGS. 6–10, a compound splint is provided which includes a primary restraining component 42 and a secondary component 44 having an intertwining surface 46 made of a fine, loose fibrous material. Similar to the application of the first embodiment, a base layer 48 is positioned on the nose 50 of a person 52 as depicted in FIG. 7. In this instance, the base layer 48 is a single tape pad shaped to overlie the nose 50, rather than a plurality of strips.

The secondary component 44 is next applied over the base layer 48, as shown in FIG. 8. As best depicted in FIG. 10, the secondary component includes the intertwining surface 46 and a first backing member 54 adhesively connected to a layer of soft, flexible foam 56. The foam 56 is adhesively connected at a face, opposite the face contacting first backing member 54, to base layer 48. As similarly described with regard to the first embodiment, either base layer 48 or foam 56 may have an adhesive coating, but it is presently preferred to provide the adhesive coating on foam 56 and protect it with a release sheet until it is to be used. Secondary component 44 is trimmed to a shape corresponding to that of the base layer 48 but of less lateral and longitudinal extent so that when applied it will not extend laterally beyond the lateral osteotomy sites. The release sheet is stripped off and foam 56 is pressed tightly against the base layer 48 to be fixedly united thereto.

As shown in FIG. 9, the primary restraining component 42 is applied over secondary component 44. Primary restraining component 42, as illustrated in FIG. 10, includes an interlacing surface 58 such as the multi-hook configuration as in the first embodiment. A second backing member 60 overlies the interlacing surface 58 and is adhesively connected to a malleable metallic panel 62 while a plastic cover 64 is united to the metallic panel 62. The exposed face of cover 64 is colored to substantially match the color of the skin of person 52. Primary component 42 is trimmed to have almost identically the same planform as secondary component 44, being a few millimeters larger laterally and longitudinally to overlie the edges of secondary component 44. Metallic panel 62 is preferably made from a sheet of soft aluminum having a thickness of the order of sixteen gauge.

Primary component 42, in its flat form, is applied to secondary component 44 in such a fashion that the vertically central portion of interlacing surface 58 contacts the vertically central portion of intertwining surface 46 so that some of the hooks engage some of the fine, loose fibers. The side portions of primary component 42 are then gently but firmly pressed inward toward the sides of the nose until it assumes the same shape, with the remainder of the hooks engaging the loose, fibrous material progressively until all of primary component 42 is securely fashioned in place. As primary component 42 is pressed into place, the edema fluid will be squeezed from the soft tissue above the bony structure of the nose. Although metallic panel 64 is malleable enough to be formed manually, it is adequately stiff enough to prevent any outward swelling or distortion of the nose during the recovery period, which would splay the bones before they begin to knit together. Thus, any swelling which occurs will be inward and therefore will not affect the healing process.

It will be apparent that the principal components of this second embodiment may also be prepared, stocked and sold in kit form in which the malleable panel 62, the interlacing surface 58, and the intertwining surface 46 are cut to a trapezoidal planform. Such a kit is substantially identical to the kit previously described with regard to the first embodiment.

The compound splint of this invention is of minimum size and has a flesh-colored exterior so that it has a minimum deleterious effect on the appearance. It is firmly secured so that it will not be displaced in ordinary activity including bathing and sleeping. Most importantly, its rigidity and secure mounting insure that it will perform its intended function properly and reliably.

The invention has been described in detail with particular reference to a plurality of embodiments thereof, but it will be understood that variations and modifications can be effected within the spirit and scope of the invention.

I claim:

1. A compound splint for application to a traumatized portion of a human body, including bones to be knitted together, a base layer of thin, flexible material coated with adhesive on at least one side and adaptable to be adhesively secured to the traumatized portion, said splint comprising:
    a secondary component having a first face adapted to be secured to the base layer and an intertwining surface formed at a second face of said secondary component; and
    a primary restraining component of malleable metallic material having an interlacing surface to anchoringly engage said intertwining surface of said secondary component, said primary restraining component being manually formable in situ to correspond to the shape of the traumatized portion and securable in place by the connection of the intertwining and interlacing formations to prevent change in the size and shape of the traumatized portion during recovery.

2. The splint, as claimed in claim 1, wherein:
    said secondary component has an area less than the area of the base layer.

3. The splint, as claimed in claim 2, wherein:
    said primary restraining component has a planform substantially identical to the planform of said secondary component.

4. The splint, as claimed in claim 1, wherein:
    said intertwining surface of said secondary component is made of a fine, loose fibrous material and said interlacing surface of said primary restraining component is made of a woven fabric having a plurality of hooks to securely engage said fine, loose, fibrous material.

5. A method of forming and applying a splint to the traumatized nose of a human being, comprising the steps of:
    applying securely to the nose a base layer;
    forming a secondary component having an intertwining surface;
    applying securely said secondary component to the exposed face of said base layer;
    forming a primary restraining component having a malleable panel and an interlacing surface;
    applying the central portion of said interlacing surface to the central portion of said intertwining surface along the dorsum of the nose; and
    pressing the side portions of said primary component inwardly toward the sides of the nose to gradually engage the remaining portions of the interlacing and intertwining surfaces to produce a desired shape and restraining effect by squeezing the edema fluid from the soft tissue of the bones to be knitted together so that these bones are not splayed apart due to swelling.

6. A nasal splint kit comprising:
    a primary restraining component including a panel of manually bendable shape-retaining sheet material and an interlacing surface formed for interconnection; and
    a secondary component having a face adaptable to be secured to the nose of a patient and including an intertwining surface formed on the face of said secondary component opposite the face securable to the nose, said interlacing surface and said intertwining surface being adaptable to detachably engage each other in facewise relation to secure said primary restraining component to said secondary component.

7. A kit, as claimed in claim 6, wherein:
    the planform of said secondary component is substantially equal to the planform of said primary component.

8. A kit, as claimed in claim 7, wherein:
    the planform of said primary restraining component and said secondary component is substantially trapezoidal.

* * * * *